United States Patent [19]

Okazaki et al.

[11] Patent Number: 5,763,453
[45] Date of Patent: Jun. 9, 1998

[54] CONDENSED INDAN DERIVATIVES AND SALTS THEREOF

[75] Inventors: Shinji Okazaki, Hanno; Tetsuji Asao, Tokorozawa; Teruhiro Utsugi, Tokyo; Yuji Yamada, Tokorozawa, all of Japan

[73] Assignee: Taiho Pharmaceutical Co., Ltd., Tokyo, Japan

[21] Appl. No.: 809,602

[22] PCT Filed: Aug. 2, 1996

[86] PCT No.: PCT/JP96/02195

§ 371 Date: Apr. 3, 1997

§ 102(e) Date: Apr. 3, 1997

[87] PCT Pub. No.: WO97/06145

PCT Pub. Date: Feb. 20, 1997

[30] Foreign Application Priority Data

Aug. 8, 1995 [JP] Japan .................................. 7-202630

[51] Int. Cl.$^6$ .................................................. C07D 221/18
[52] U.S. Cl. .................................................. 514/284; 546/61
[58] Field of Search ................................. 514/284; 546/61

[56] References Cited

U.S. PATENT DOCUMENTS

| | | | |
|---|---|---|---|
| 3,912,740 | 10/1975 | Zee-Cheng et al. | 546/48 |
| 3,985,899 | 10/1976 | Svoboda | 514/285 |
| 4,014,885 | 3/1977 | Zee-Cheng et al. | 546/48 |
| 4,826,850 | 5/1989 | Yamato | 514/284 |
| 4,918,077 | 4/1990 | Behrens | 514/284 |
| 4,939,158 | 7/1990 | Fendreich et al. | 514/284 |
| 5,223,506 | 6/1993 | Luzzio et al. | 514/279 |
| 5,597,831 | 1/1997 | Michalsky et al. | 514/284 |

OTHER PUBLICATIONS

Yominaga, Y. et al, 'Reaction of Enaminones with Carbon Disulfide: Synthesis of Heterocycles Using Enamino Dithiocarboxylates' J. Heterocycl. Chem. 1991, 28(5), pp. 1245–1255.

Krontriris, T.G. 'Molecular and Cellular Biology of Cancer' in Internal Medicine, 4th ed, editor Jay Stein, 1995, pp. 699–715.

Pazdur, R. et al, 'Correlation of Murine Antitumor Models in Predicting Cinical Drug Activity in Non–Small Cell Lung Cancer: A Six Year Experience'Proc. Am. Soc. Clin. Oncol. 1984, 3, p. 219.

Martin, D.S. et al, 'Role of Murine Tumor Models in Cancer Treatment Research' Cancer Research, 1986, 46, pp. 2189–2192.

J. Heterocycl chem., vol. 28 (5), pp. 1165–1468 (1991).

Jour. Indian Chem. Soc., vol. 44, No. 12, 1001–1004 (1967).

Pol. J. Pharmacol. Pharm., 35, 327–332 (1983).

Pol. J. Pharmacol. Pharm., 35, 523–530 (1983).

Pol. J. Pharmacol. Pharm., 38, 221–227 (1986).

Polish Journal of Chemistry, 55, 121–128 (1981).

Chemical Abstracts vol. 99, 1983, p. 606 99: 22335j (Polish PL 116, 879).

*Primary Examiner*—C. Warren Ivy
*Assistant Examiner*—Garth M. Dahlen
*Attorney, Agent, or Firm*—Nikaido, Marmelstein Murray & Oram LLP

[57] ABSTRACT

A condensed indan derivative represented by the formula (1)

wherein the ring A is an optionally substituted benzene ring or a benzene ring which has lower alkylenedioxy group(s), the ring B is an optionally substituted benzene ring or a benzene ring which has lower alkylene dioxy group(s), and R is a group —$NR_1R_2$, an optionally substituted nitrogen-containing heterocyclic group, a group —$OR_3$ or a group —$SR_4$ (wherein $R_1$ and $R_2$ are the same or different and each represent a hydrogen atom, a phenyl group, an optionally substituted nitrogen-containing heterocyclic group, or a lower alkyl group which may be substituted by optionally substituted amino group(s), lower alkoxy group(s), phenyl group(s), nitrogen-containing heterocyclic group(s) or hydroxyl group(s), and $R_3$ and $R_4$ each represent a lower alkyl group which may be substituted by substituted amino group(s)), provided that at least one of the rings A and B is a substituted benzene ring and R is not —$NHCH_3$, and salts thereof, and medical use of said derivative and salts.

8 Claims, No Drawings

CONDENSED INDAN DERIVATIVES AND SALTS THEREOF

This application is a 371 of PCT/JP96/02195 filed Aug. 2, 1996.

TECHNICAL FIELD

The present invention relates to novel condensed indan derivatives and salts thereof. The compounds of the invention have excellent antitumor activity and are useful as antitumor agents.

BACKGROUND ART

Conventionally known 11H-indeno[1,2-b]quinolin-11-one derivatives which have a skeleton similar to that of the compound of the present invention include, for example, compounds disclosed in Pol. J. Chem., 55, 121–128 (1981), Pol. J. Pharmacol. Pharm., 35 327–332 (1983), ibid., 35 523–530 (1983) and ibid., 38 221–227 (1986). Specifically stated, these documents disclose compounds substituted at the 10-position by a lower alkylamino group which may have a substituent, a phenylamino group, etc. These documents, however, refer to only anti-inflammatory and analgetic effects as pharmacological activity of said compounds, and do not report or disclose antitumor activity. Accordingly, the antitumor activity of the condensed indan derivatives of the present invention has not been found yet.

An object of the present invention is to provide a compound which has excellent antitumor activity and is useful as a therapeutic agent for tumors. Another object of the invention is to provide the use of said compound or salts thereof as an antitumor agent, and a method for treating tumors using said compound or a salt thereof. A further object of the invention is to provide a method for preparing said compound.

DISCLOSURE OF THE INVENTION

The inventors of the present invention conducted extensive research and found that condensed indan derivatives have excellent antitumor activity and are useful as antitumor agents. The present invention has been accomplished based on this finding.

The present invention provides a condensed indan derivative represented by the formula (1):

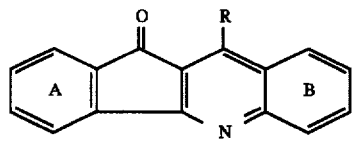

wherein the ring A is an optionally substituted benzene ring or a benzene ring which has lower alkylenedioxy group(s), the ring B is an optionally substituted benzene ring or a benzene ring which has lower alkylenedioxy group(s), and R is a group —$NR_1R_2$, an optionally substituted nitrogen-containing heterocyclic group, a group —$OR_3$ or a group —$SR_4$ (wherein $R_1$ and $R_2$ are the same or different and each represent a hydrogen atom, a phenyl group, an optionally substituted nitrogen-containing heterocyclic group, or a lower alkyl group which may be substituted by optionally substituted amino group(s), lower alkoxy group(s), phenyl group(s), nitrogen-containing heterocyclic group(s) or hydroxyl group(s), and $R_3$ and $R_4$ each represent a lower alkyl group which may be substituted by substituted amino group(s)), provided that at least one of the rings A and B is a substituted benzene ring and R is not —$NHCH_3$, or a salt thereof.

The compound of the present invention represented by the formula (1) has excellent antitumor activity and is useful for treating various tumors.

The present invention provides a composition comprising an effective amount of the compound of the formula (1) or a phamaceutically acceptable salt thereof and a pharmaceutical carrier.

In particular, the present invention provides an antitumor agent comprising an effective amount of the compound of the formula (1) or a pharmaceutically acceptable salt thereof and a pharmaceutical carrier.

The present invention further provides a method for treating tumors in mammals comprising administering to mammals an effective amount of the compound of the formula (1) or a pharmaceutically acceptable salt thereof.

The groups represented by R, $R_1$, $R_2$, $R_3$ and $R_4$ and other groups shown in the present specification are described below more specifically.

Examples of the substituents in the benzene rings represented by the rings A and B include a halogen atom, a lower alkyl group, a lower alkoxy group, a hydroxyl group, a nitro group, an amino group, a lower acyloxy group, a benzyloxy group, a lower acylamino group, a cyano group, a carboxyl group, a lower alkoxycarbonyl group, etc. Among them, a lower alkoxy group and a hydroxyl group are preferred.

Said substituents may be at any positions of each ring and are the same or different. Each of the rings may have 1 to 4 substituents. Preferred positions are the 2- and/or 3-positions in the case the ring A, and 7- and/or 8-positions in the case of the ring B. Preferably, each of the rings A and B has 0 to 2 substituents.

Particularly preferred are compounds in which one of the rings A and B has 1 or 2 substituents and the other has no substituents.

Table 1 given later shows the structure of the indeno[1, 2-b]quinoline ring and the positions of the substituents in the rings A and B.

Examples of the lower alkylenedioxy group for use in the present invention include $C_{1-4}$ alkylenedioxy groups such as methylenedioxy, ethylenedioxy, trimethylenedioxy and tetramethylenedioxy. The positions of these substituents are preferably selected so as to form a 1,2- or 2,3-substituted indeno[1,2-b]quinoline ring in the case of the ring A, while in the case of ring B, the positions are selected so as to form a 7,8- or 8,9-substituted indeno[1,2-b]quinoline ring.

Examples of the halogen atom include fluorine, chlorine, bromine and iodine.

The lower alkyl group for use in the present invention includes, for example, straight- or branched-chain $C_{1-6}$ alkyl groups such as methyl, ethyl, n-propyl, isopropyl, n-butyl, isobutyl, sec-butyl, tert-butyl, pentyl, hexyl, etc.

The lower alkoxy group includes, for example, straight- or branched-chain $C_{1-6}$ alkoxy groups such as methoxy, ethoxy, n-propoxy, isopropoxy, n-butoxy, isobutoxy, sec-butoxy, tert-butoxy, pentyloxy, hexyloxy, etc.

The lower acyloxy group includes, for example, straight- or branched-chain $C_{1-6}$ acyloxy groups such as formyloxy, acetoxy, propionyloxy, butyryloxy, 2-methylpropionyloxy, pivaloyloxy, pentanoyloxy, 3-methylbutyryloxy, hexanoyloxy, etc.

The lower acylamino group includes, for example, straight- or branched-chain $C_{1-6}$ acylamino groups such as formylamino, acetylamino, propionylamino, butyrylamino, 2-methylpropionylamino, pivaloylamino, pentanoylamino, 3-methylbutyrylamino, hexanoylamino, etc.

The lower alkoxycarbonyl group includes, for example, straight- or branched-chain $C_{2-7}$ alkoxycarbonyl groups such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl, hexyloxycarbonyl, etc.

Examples of the substituents in the nitrogen-containing heterocyclic group represented by R, $R_1$ and $R_2$ include a lower alkyl group, a lower alkyl group which has a hydroxyl group, a phenyl group, a nitrogen-containing heterocyclic group, etc., among which a lower alkyl group and a piperidino group are preferred.

As to the "optionally substituted amino group(s)" in the definitions of $R_1$ and $R_2$ and "a lower alkyl group which may be substituted by substituted amino group(s)" represented by $R_3$ and $R_4$, examples of the substituents in the substituted amino group include lower alkyl, lower cycloalkyl, di-lower alkylamino-alkyl, hydroxy-lower alkyl, benzyloxycarbonyl, lower acyl, etc. Among them, preferred is lower alkyl. The amino group may be either mono- or di-substituted, but a di-substituted amino group is preferred.

The lower alkyl group which has substituted amino group (s) includes, for example, mono- or di-alkylaminoalkyl groups wherein the alkyl moiety has 1 to 6 carbon atoms, such as methylaminomethyl, ethylaminomethyl, methylaminoethyl, ethylaminoethyl, dimethylaminomethyl, dimethylaminoethyl, dimethylaminopropyl, diethylaminomethyl, diethylaminoethyl, diethylaminopropyl, diethylaminobutyl, diethylaminopenta-2-yl, dipropylaminoethyl, dibutylaminoethyl, dibutylaminohexyl, etc.; alkyl groups substituted by $C_{2-6}$ acylamino group(s), such as N-dimethylaminoethyl-N-methylaminoethyl, acetylaminoethyl, acetylaminopropyl, propionylaminoethyl, propionylaminopropyl, pivaloylaminoethyl, pivaloylaminopropyl, etc.; alkyl groups substituted by a $C_{3-6}$ cycloalkylamino group, such as cyclopropylaminomethyl, cyclopentylaminomethyl, cyclopentylaminoethyl, cyclohexylaminomethyl, cyclohexylaminoethyl, etc.; alkyl groups substituted by a $C_{1-4}$ hydroxyalkylamino group, such as hydroxymethylaminomethyl, 2-hydroxyethylaminomethyl, 3-hydroxypropylaminomethyl, hydroxymethylaminoethyl, 2-hydroxyethylaminoethyl, 3-hydroxypropylaminoethyl, 4-hydroxybutylaminoethyl, etc.; alkyl groups substituted by a benzyloxycarbonylamino group, such as benzyloxycarbonylaminomethyl, benzyloxycarbonylaminoethyl, N-benzyloxycarbonyl-N-methylaminoethyl, etc.; and the like.

The lower alkyl group which has lower alkoxy group(s) includes, for example, straight- or branched-chain $C_{1-6}$ alkyl groups substituted by a $C_{1-6}$ alkoxy group, such as methoxymethyl, ethoxymethyl, propoxymethyl, methoxyethyl, ethoxyethyl, methoxypropyl, etc.

The lower alkyl group which has phenyl group(s) includes, for example, straight- or branched-chain $C_{1-4}$ alkyl group containing 1 to 3 phenyl groups, such as benzyl, phenethyl, 2-phenethyl, phenylpropyl, benzhydryl and trityl.

The nitrogen-containing heterocyclic group represented by R, $R_1$ and $R_2$ is preferably 5- or 6-membered monocyclic heterocyclic group which has 1 to 4 nitrogen atoms and 0 or 1 oxygen or sulfur atom. Examples of said group include pyrrolyl, oxazolyl, thiazolyl, isoxazolyl, isothiazolyl, pyrazolyl, imidazolyl, oxadiazolyl, thiadiazolyl, triazolyl, oxatriazolyl, thiatriazolyl, tetrazolyl, pyridyl, pyridazinyl, pyrimidinyl, pyradinyl, pyrrolidinyl, pyrrolinyl, imidazolidinyl, imidazolinyl, pyrazolidinyl, pyrazolinyl, piperidyl, piperidino, piperadinyl, morpholinyl, morpholino, etc. Among them, preferred are 5- or 6-membered monocyclic heterocyclic groups which have 1 to 3 nitrogen atoms and 0 or 1 oxygen atom. Particularly preferred are pyridyl, pyrrolidinyl, piperidyl, piperidino, piperadinyl, morpholinyl, morpholino and 1,2,4-triazolyl, and more preferred are pyrrolidinyl, piperidino and piperadinyl.

The optionally substituted nitrogen-containing heterocyclic group includes, for example, 4-methylpiperadinyl, 4-ethylpiperadinyl, 4-phenylpiperadinyl, 4-methylpiperidino, 4-ethylpiperidino, 4-piperidinopiperidino, etc.

The lower alkyl group which has nitrogen-containing heterocyclic group(s) represented by $R_1$ and $R_2$ includes, for example, straight- or branched-chain $C_{1-6}$ alkyl groups containing a nitrogen-containing heterocyclic group, such as 2-pyridylmethyl, 3-pyridylmethyl, 4-pyridylmethyl, 2-pyridylethyl, 3-pyridylethyl, 4-pyridylethyl, pyrrolidinylmethyl, pyrrolidinylethyl, piperidinomethyl, piperidinoethyl, piperidinylmethyl, piperidinylethyl, morpholinomethyl, morpholinoethyl, etc. Among them, preferred are pyrrolidinylmethyl and pyrrolidinylethyl.

The lower alkyl group which has hydroxyl group(s) includes, for example, straight- or branched-chain $C_{1-6}$ alkyl groups containing 1 or 2 hydroxyl groups, such as hydroxymethyl, 1-hydroxyethyl, 2-hydroxyethyl, 2-hydroxypropyl, 3-hydroxypropyl, 2,3-dihydroxypropyl, 4-hydroxybutyl, 2,3-dihydroxybutyl, 5-hydroxypentyl, 2,3-dihydroxypentyl, 6-hydroxyhexyl, 2,3-dihydroxyhexyl, etc.

The salts of the compound of the present invention are not limited specifically insofar as they are pharmaceutically acceptable, and include, for example, salts of organic acids such as formic acid, acetic acid, propionic acid, trifluoroacetic acid, tartaric acid, malic acid, maleic acid, fumaric acid, succinic acid, oxalic acid, methanesulfonic acid, p-toluenesulfonic acid, etc. and salts of inorganic acids such as hydrochloric acid, hydrobromic acid, sulfuric acid, phosphoric acid, etc.

In the compound of the formula (1), the ring A is preferably an unsubstituted or hydroxyl- or lower alkoxy-substituted benzene ring, more preferably an unsubstituted or hydroxyl-substituted benzene ring.

The ring B is preferably an unsubstituted or hydroxyl- or lower alkoxy-substituted benzene ring, more preferably an unsubstituted or hydroxyl-substituted benzene ring.

R is preferably a group $-NR_1R_2$ or $-OR_3$, particularly $-NR_1R_2$.

In the group $-NR_1R_2$, $R_1$ and $R_2$ are the same or different, and preferably, they each represent a hydrogen atom or a lower alkyl group which may be substituted by substituted amino group(s) or nitrogen-containing heterocyclic group(s). More preferably, $R_1$ and $R_2$ each represent a hydrogen atom or a lower alkyl group which may be substituted by a di-lower alkyl-substituted amino group or a pyrrodinyl group, and still more preferably, $R_1$ is a lower alkyl group substituted by a dimethylamino group, a diethylamino group or a pyrrolidinyl group and $R_2$ is a hydrogen atom.

$R_3$ and $R_4$ are preferably a lower alkyl group which may be substituted by a di-lower alkyl-substituted amino group.

Preferred species of the compound of the present invention are those of the formula (1) wherein the ring A is an unsubstituted or hydroxyl- or lower alkoxy-substituted benzene ring, the ring B is an unsubstituted or hydroxyl- or lower alkoxy-substituted benzene ring (provided that at least one of the rings A and B is a substituted benzene ring), R is $-NR_1R_2$ (wherein $R_1$ and $R_2$ are the same or different and each represent a hydrogen atom or a lower alkyl group which may be substituted by a substituted amino group or a nitrogen-containing heterocyclic group) other than $-NHCH_3$, or $-OR_3$ (wherein $R_3$ is a lower alkyl group which may be substituted by a di-lower alkyl-substituted amino group).

More preferred species are compounds of the formula (1) wherein the ring A is an unsubstituted or hydroxyl-substituted benzene ring, the ring B is an unsubstituted or hydroxyl-substituted benzene ring (provided that at least one of the rings A and B is a substituted benzene ring), R is $-NR_1R_2$ (wherein $R_1$ and $R_2$ are the same or different and each represent a hydrogen atom, or a lower alkyl group which may be substituted by a di-lower alkyl-substituted amino group or a pyrrolidinyl group) other than $-NHCH_3$, and in particular, $R_1$ is a lower alkyl group substituted by a dimethylamino group, a diethylamino group or a pyrrolidinyl group, and $R_2$ is a hydrogen atom).

As used herein "lower alkyl group which may be substituted by a di-lower alkyl-substituted amino group or a pyrrolidinyl group" means "a lower alkyl group which may be substituted by a di-lower alkyl-substituted amino group, or a lower alkyl group which may be substituted by a pyrrolidinyl group".

The compound of the present invention represented by the formula (1) can be produced, for example, according to the following reaction scheme 1.

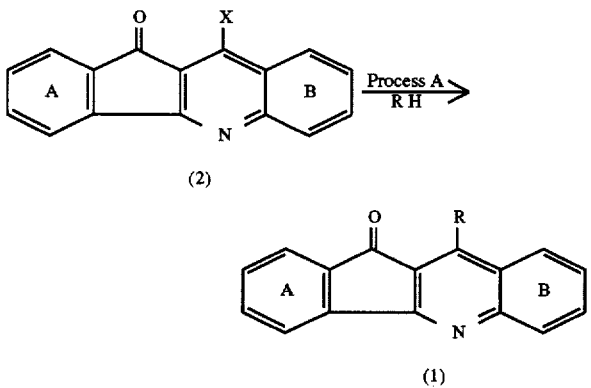

wherein the rings A and B and R are as defined above, X is a halogen atom and RH is an amine [$NH(R_1)(R_2)$] or a nitrogen-containing heterocyclic compound which may have substituent(s)], alcohol ($R_3OH$) or thiol ($R_4SH$) (wherein $R_1$, $R_2$, $R_3$ and $R_4$ are as defined above).
[Process A]

The 10-halogenoindeno[1,2-b]quinolin-11-one derivative of the formula (2) is aminated, alkoxylated or thioxylated using the amine represented by RH [$NH(R_1)(R_2)$ or a nitrogen-containing heterocyclic compound which may have substituent(s)], alcohol ($R_3OH$) or thiol ($R_4SH$), respectively, without using solvents or in an appropriate solvent, whereby the compound of the present invention represented by the formula (1) is obtained.

For the amination, sodium hydride, tert-butoxypotassium, sodium hydroxide, potassium hydroxide, potassium carbonate, sodium carbonate, sodium bicarbonate, triethylamine, etc. may be employed without using solvents or in an appropriate solvent. For alkoxylation, the alcohol may be used as such or as an alcoholate prepared by adding sodium, sodium hydride, tert-butoxypotassium, etc. in an appropriate solvent. Thiol for the thioxylation may be used as such or as a thiolate prepared by adding sodium hydride, sodium hydroxide, potassium carbonate, triethylamine, etc.

Examples of the solvent include alcohols such as methanol, ethanol, propanol, tert-butanol, etc., dimethylformamide, dimethylacetoamide, pyridine, toluene, benzene, acetonitrile, tetrahydrofuran, water, etc. These solvents can be used singly or as a mixture of two or more.

For the reaction, it is suitable to use the amine, alcohol or thiol in a proportion of 0.1 to 100 moles, preferably 1 to 10 moles per mole of the compound of the formula (2). The reaction advantageously proceeds at a reaction temperature of 0° to 200° C., preferably 20° to 150° C., for a reaction period of 0.1 to 100 hours, preferably 0.5 to 60 hours.

When the compound of the formula (1) produced according to the reaction scheme 1 has lower alkoxy group(s) or benzyloxy group(s) in the ring A or B, the substituent can be converted into hydroxyl group(s) when necessary, for example by the reaction with a inorganic acid such as hydrobromic acid, hydroiodic acid, hydrochloric acid, sulfuric acid or the like without using solvents or in an appropriate solvent. Examples of the solvent include acetic acid, water, etc., which can be used singly or as a mixture of two or more. For the reaction, the hydrobromic acid, hydroiodic acid, hydrochloric acid, sulfuric acid or the like is used in a proportion of 1 to 100 parts (v/w), preferably 5 to 100 parts (v/w), per part of the compound of the formula (1) substituted by lower alkoxy group(s) or benzyloxy group(s). The reaction advantageously proceeds at a reaction temperature of 0° to 200° C., preferably 50° to 150° C., for a reaction period of 0.1 to 100 hours, preferably 0.5 to 60 hours.

When the compound of the formula (1) produced according to the reaction scheme 1 has hydroxyl group(s) in the ring A or B, the substituent can be converted into alkoxyl, benzyloxy or acyloxy group(s) by alkylation, benzylation or acylation, respectively, if necessary.

The alkylation or benzylation is carried out by reacting the compound with an alkylating agent or a benzylating agent, respectively, in an appropriate solvent in the presence of a base. Examples of the solvent include dimethoxyethane, dioxane, tetrahydrofuran, dimethylformamide, acetone, etc. Examples of the base are potassium carbonate, sodium carbonate, potassium hydroxide, etc. The alkylating agent is, for example, halide, sulfuric acid ester or sulfonic acid ester of optionally substituted alkane, and the like. Examples of the benzylating agent include benzyl halide and the like. The proportions of the base and alkylating or benzylating agent in the reaction system are 1 to 5 moles of the base and 1 to 5 moles of the alkylation or benzylating agent per mole of the hydroxyl group. The reaction advantageously proceeds at a reaction temperature of 0° to 80° C. for a reaction period of 0.1 to 24 hours, preferably 0.5 to 10 hours.

The acylation is carried out by reacting the compound with a desired carboxylic acid or a reactive derivative thereof. When a reactive derivative is used, the reaction is carried out in an appropriate solvent, and a suitable base may be added to accelerate the reaction, although dependent on the kind of the reactive derivative and the starting phenolic derivative. Such reactive derivative includes, for example, acid anhydrides, acid anhydride mixtures, acid halides and the like. Examples of the solvent include chloroform, dichloromethane, dioxane, tetrahydrofuran, dimethylformamide, pyridine, etc. Examples of the base include sodium bicarbonate, potassium bicarbonate, triethylamine, pyridine, 4-dimethylaminopyridine, etc. The proportions of the base and acylating agent in the reaction system are 1 to 5 moles of the former and 1 to 5 moles of the latter per mole of the hydroxyl group. The reaction advantageously proceeds at a reaction temperature of 0° to 50° C. for a reaction period of 0.1 to 24 hours, preferably 0.5 to 3 hours.

The compound of the present invention produced by the above reaction can be made into a salt by a conventional process, for example by reacting the compound in an appropriate solvent with an organic acid such as formic acid, acetic acid, propionic acid, trifluoroacetic acid, tartaric acid, malic acid, maleic acid, fumaric acid, succinic acid, oxalic acid, methanesulfonic acid, p-toluenesulfonic acid or the like, or an inorganic acid such as hydrochloric acid, hydrobromic acid, sulfuric acid, phosphoric acid or the like, as mentioned above. Examples of the solvent include water, methanol, ethanol, dichloromethane, tetrahydrofuran, etc. The reaction temperature is preferably 0° to 50° C.

The 10-halogeno-11H-indeno[1,2-b]quinolin-11-one derivative of the formula (2) used as the starting material in the reaction scheme 1 can be produced, for example by the process described in Pol. J. Chem., 55 121–128 (1981). Specifically stated, said compound can be produced according to the following reaction scheme 2, for instance.

<Reaction Scheme>

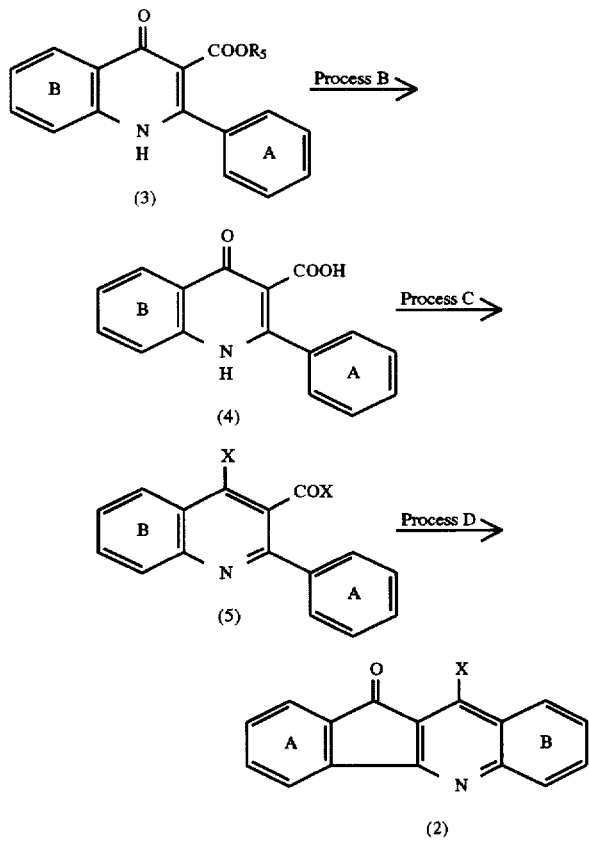

wherein the rings A and B and X are as defined above, and $R_5$ is a lower alkyl group.

[Process B]

The compound of the formula (3) is hydrolyzed with a basic compound usually in an appropriate solvent to produce the carboxylic acid of the formula (4).

The compound of the formula (3) can be produced by the process described in Berichte 18 2632 (1885) using the benzoyl halide compound (ring A) and the aniline derivative (ring B) as starting materials.

The solvent is not limited specifically insofar as it does not participate in the reaction. Examples are alcohols such as methanol, ethanol, propanol, etc., ethers such as dioxane, tetrahydrofuran, dimethoxyethane, etc., water, and the like. These solvents can be used singly or as a mixture of two or more. Examples of the basic compound include hydroxides of alkali metals such as sodium hydroxide, potassium hydroxide, etc. and hydroxides of alikali earth metals such as barium hydroxide, etc.

For the reaction, the basic compound is used in a proportion of 1 to 10 moles per mole of the compound of the formula (3). The reaction advantageously proceeds at a reaction temperature of 0° to 100° C., preferably 50° to 100° C. for a reaction period of 0.1 to 100 hours, preferably 1 to 50 hours.

[Process C]

The compound of the formula (4) obtained by the process B is reacted with a halogenating agent usually without using solvents or, when necessary, in an inert solvent to produce the compound of the formula (5).

The inert solvent for use in the reaction is not specifically limited insofar as it does not participated in the reaction. Examples are chloroform, benzene, toluene, xylene, etc. Examples of the halogenating agent include thionyl chloride, thionyl bromide, phosphorus oxychloride, phosphorus trichloride, phosphorus tribromide, phosphorus pentachloride, phosphorus pentabromide, etc. For accelerating the reaction, pyridine, dimethylformamide or the like may be added.

For the reaction, the halogenating agent is preferably used in a proportion of 1 to 100 moles per mole of the compound of the formula (4). The reaction advantageously proceeds at a reaction temperature of 0° to 200° C., preferably 50° to 150° C., for a reaction period of 0.5 to 100 hours, preferably 0.5 to 10 hours.

The compound of the formula (5) obtained by the reaction can be isolated and purified when necessary, but can be used for the subsequent process without being purified.

[Process D]

The compound of the formula (5) obtained by the process C is reacted with protonic acid or Lewis acid without using solvents or, when necessary, in an inert solvent to produce the compound of the formula (2).

The inert solvent for use in the reaction is not limited specifically insofar as it does not participate in the reaction. Examples are nitrobenzene, xylene, dichloromethane, carbon tetrachloride, etc. Examples of protonic acid are sulfuric acid, phosphoric acid, polyphosphoric acid, hydrogen bromide, etc., and examples of Lewis acid are aluminum chloride, tin chloride, iron chloride, etc.

When protonic acid is used, the proportion thereof is 1 to 1000 parts (v/w), preferably 3 to 100 parts (v/w) per part of the compound of the formula (5), whereas when Lewis acid is used, the proportion thereof is 1 to 100 moles, preferably 1 to 10 moles per mole of the compound of the formula (5). The reaction advantageously proceeds at a reaction temperature of 0° to 200° C., preferably 20° to 150° C., for a reaction period of 0.5 to 50 hours, preferably 0.5 to 20 hours.

The compounds of the present invention and the other compounds obtained above can be isolated and purified by conventionally known processes for isolation and purification, such as concentration, extraction with a solvent, filteration, recrystallization, various types of chromatography, etc.

When the compound of the formula (1) of the invention is used as an agent for treating malignant tumors of mammals including humans (subjects), various pharmaceutical dosage forms can be employed in accordance with the purposes. Specifically stated, the dosage forms include, for example, oral preparations such as tablets, coated tablets, pills, powders, granules, capsules, solutions, suspensions and emulsions, etc., and non-oral preparations such as injections, suppositories, ointments and plasters. These preparations are formulated in a manner conventionally known in the art.

Carriers which are usable for the formulation of tablets includes, for example, excipients such as lactose, sucrose, sodium chloride, glucose, urea, starch, calcium carbonate, kaolin, crystalline cellulose, silicic acid, etc., binders such as simple syrup, glucose solution, starch solution, gelatin solution, carboxymethyl cellulose, shellac, methyl cellulose, potassium phosphate, polyvinylpyrrolidone, etc., disintegrators such as dried starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, lactose, etc., disintegration preventing agents such as sucrose, stearic acid, cacao butter, hydrogenated oils, etc., absorption promoting agents such as quaternary ammonium base, sodium lauryl sulfate, etc., humectants such as glycerin, starch, etc., adsorbents such as starch, lactose, kaolin, bentonite, colloidal silicic acid, etc., lubricants such as purified talc, stearic acid salts, boric acid powder, polyethylene glycol, etc., and the like. The tablets may be further processed into coated tablets using an ordinary coating film, for example sugar coated tablets, gelatin coated tablets, film coated tablets, etc., and may be double-layered tablets, multilayered tablets and the like.

For the formulation of pills, usable carriers include, for example, excipients such as glucose, lactose, starch, cacao butter, hardened vegetable oils, kaolin, talc, etc., binders such as gum arabic powder, tragacanth powder, gelatin, etc., disintegrators such as laminaran, agar, etc., and the like.

Capsules are usually prepared by mixing the compound of the present invention with the above-mentioned various carriers and enclosing the mixture into hardened gelatin capsules, soft capsules or the like.

For the formulation of suppositories, carriers can be used which include, for example, polyethylene glycol, cacao butter, higher alcohols, esters of higher alcohols, gelatin, semisynthetic glyceride, etc.

For the formulation of injections, the solutions, emulsions and suspensions are preferably sterilized and isotonic with blood. For producing these forms, diluents can be employed which include, for example, water, ethyl alcohol, macrogol, propylene glycol, ethoxylated isostearyl alcohol, polyoxylated isostearyl alcohol, polyoxyethylene sorbitan fatty acid esters, etc. In this procedure, sodium chloride, glucose or glycerin may be incorporated into the pharmaceutical preparation in an amount sufficient to provide isotonic solutions. Conventional solubilizing agents, buffers, soothing agents and the like may be also added.

Ointments can be prepared in a usual manner by adding, to the compound of the invention, conventionally used bases, stabilizers, lubricants, preservative, etc. when necessary. Examples of useful bases are liquid paraffin, white petrolatum, bleached beeswax, paraffin, etc. Usable preservatives include methyl para-hydroxybenzoate, ethyl para-hydroxybenzoate, propyl para-hydroxybenzoate, etc.

Plasters can be prepared in a usual manner by applying said ointments, pastes, creams, gels, etc. to an ordinary support. Examples of the suppports include woven fabrics or non-woven fabrics composed of cotton, staple fibers, chemical fibers or the like; films or foamed sheets made from non-rigid polyvinyl chloride, polyethylene, polyurethane or the like; etc.

When required, the above preparations may contain pharmaceutically acceptable additives, such as coloring agents, preservatives, perfumes, flavors, sweeteners, etc., other medicaments and the like.

The amount of the compound of the invention to be incorporated in the pharmaceutical preparation is not specifically limited and can be selected from a wide range. A suitable amount is in the range of 1 to 70% by weight based on the pharmaceutical preparation.

The mode of administration is not specifically limited and is suitably determined according to the dosage form, patients' age, sex and other factors, the severity of diseases, etc. For example, tablets, pills, solutions, suspensions, emulsions, granules and capsules are orally administered. Injections are intravenously administered singly or in mixture with conventional parenteral fluids such as glucose, amino acid, etc. or may be administered intramuscularly, intracutaneously, subcutaneously or intraperitoneally. Suppositories are applied into the rectum. Ointments are applied to the skin, mucous membrane in the buccal cavity, or the like.

The amount of the compound of the invention in each dosage unit of the above forms depends on the conditions of the patient to be treated, the particular dosage form selected and other factors. Generally, preferred amounts per dosage unit are about 1 to about 1,000 mg for oral preparations, about 0.1 to about 500 mg for injections, and about 5 to about 1,000 mg for suppositories. The daily dosage of the pharmaceutical preparation in any of the forms mentioned above is also dependent on the patients' condition, body weight, age, sex and other factors, but it is generally recommendable to administer about 0.1 to about 5,000 mg, preferably about 1 to about 1,000 mg, per day for an adult patient, either in a single dose or in 2 to 4 divided doses.

The malignant tumors to be treated with the pharmaceutical preparation containing the compound of the invention are not specifically limited and include, for example, cancers of the head and neck, esophagus, stomach, colon, rectum, liver, gall bladder-bile duct, pancreas, lung, breast, ovary, urinary bladder, prostate, testis, cervix uteri, skin and other parts, osteosarcoma or sarcoma of soft part, malignant lymphoma, leukemia, cerebral tumor, etc.

Best Mode for Carrying out the Invention

Reference Examples, Examples and Pharmacological Test Example are given below to illustrate the present invention in further detail.

Reference Example 1

Synthesis of 1,4-dihydro-2-(4-methoxyphenyl)-4-oxo-3-quinolinecarboxylic acid

A mixture of 7.0 g (21.6 mmol) of 1,4-dihydro-4-(4-methoxyphenyl)-4-oxo-3-quinolinecarboxylic acid ethyl ester, 17.5 ml of ethanol, 52.5 ml of water and 6.1 g (108 mmol) of potassium hydroxide was refluxed with heating for 10 hours. After completion of the reaction, the reaction mixture was made acid with 25 ml of 6N hydrochloric acid and filtered to collect precipitated crystals. The obtained crystals were washed with ethanol-diethylether, giving 6.0 g of the title compound (yield: 93.9%).

m.p.: >300° C.

$^1$H-NMR (DMSO-$d_6$) δ: 12.87 (1H.s), 8.30 (1H, d, J=8 Hz), 7.91–7.82 (2H, m), 7.58 (1H, d-d-d, J=8, 7, 2 Hz), 7.49 (2H, d, J=9 Hz), 7.07 (2H, d, J=9 Hz), 3.85 (3H, s)

IR(KBr)cm$^{-1}$: 2930, 1688, 1634, 1608, 1517, 1507, 1472, 1447, 1257

Reference Example 2

Synthesis of 10-chloro-2-methoxy-11H-indeno[1,2-b]quinolin-11-one

A mixture of 5.5 g (18.6 mmol) of 1,4-dihydro-2-(4-methoxyphenyl)-4-oxo-3-quinolinecarboxylic acid obtained in Reference Example 1 and 55 ml (0.59 mol) of phosphorous oxychloride was refluxed with heating for 5 hours in the presence of a catalytic amount of N,N-dimethylformamide. After completion of the reaction, the reaction mixture was evaporated to dryness, and the residue was washed several times with n-hexane. 55 g of polyphosphoric acid was added to the washed residue, and the mixture was stirred for 2 hours with heating at 130° C. After completion of the reaction, the reaction mixture, while hot, was added to ice water, and precipitated crystals were collected by filtration. The obtained crystals were washed with water and ethanol and dissolved in a large amount of chloroform. The solution was filtered to remove insoluble matter and evaporated to dryness and recrystallized from toluene, giving 2.7 g of the title compound (yield: 49.0%).

m.p.: 216°–218° C.

$^1$H-NMR (DMSO-$d_6$) δ: 8.23 (1H, d-d, J=8, 1 Hz), 8.02 (1H, d-d, J=8, 1 Hz), 7.90–7.84 (2H, m), 7.68 (1H, d-d-d, J=8, 7, 1 Hz), 7.29 (1H, d-d, J=8, 3 Hz), 7.24 (1H, d, J=2 Hz), 3.90 (3H, s)

IR(KBr)cm$^{-1}$: 1720, 1616, 1604, 1583, 1567, 1513, 1493, 1365, 1287, 1240, 797, 760

Reference Example 3

Synthesis of 10-chloro-8-methoxy-11H-indeno[1,2-b]quinolin-11-one

A mixture of 3.5 g (10.8 mmol) of 1,4-dihydro-6-methoxy-4-oxo-2-phenyl-3-quinolinecarboxylic acid ethyl ester, 4.5 g (21.6 mmol) of phosphorus pentachloride and 100 ml of benzene was stirred at room temperature for 1 hour and then refluxed with heating for 2 hours. After completion of the reaction, the reaction mixture was evaporated to dryness, and the residue was crystallized from n-hexane. The obtained crystals were collected by filteration and dried under reduced pressure, giving 3.2 g of 4-chloro-6-methoxy-2-phenyl-3-quinolinecarboxylic acid chloride (yield: 89.2%). 2.7 g (8.1 mmol) of the obtained acid chloride was added to 27 g of polyphosphoric acid heated to 90° C., and the mixture was stirred for 4 hours with heating at 130° C. After completion of the reaction, the reaction mixture, while hot, was added to ice water, and precipitated crystals were collected by filteration. The obtained crystals were dissolved in chloroform, and the solution was filtered to remove insoluble matter. The chloroform was distilled off, and the residue was recrystallized from benzene, giving 0.8 g of the title compound (yield: 33.4%).

m.p.: 232°–234° C.

$^1$H-NMR (CDCl$_3$) δ: 8.04 (1H, d, J=8 Hz), 8.02 (1H, d, J=9 Hz), 7.84 (1H, d, J=7 Hz), 7.68 (1H, d-d-d, J=8, 7, 1 Hz), 7.62 (1H, d, J=3 Hz), 7.51 (1H, d-d-d, J=8, 7, 1 Hz), 7.44 (1H, d-d, J=9, 3 Hz), 4.00 (3H, s)

IR(KBr)cm$^{-1}$: 1718, 1621, 1614, 1514, 1239, 847, 831, 761, 724

Reference Example 4

Synthesis of 10-chloro-8-hydroxy-11H-indeno[1,2-b]quinolin-11-one

A mixture of 500 mg (1.5 mmol) of 4-chloro-6-methoxy-2-phenyl-3-quinolinecarboxylic acid chloride obtained in Reference Example 3 and 10 ml of sulfuric acid was stirred for 3 hours with heating at 130° C. After completion of the reaction, the reaction mixture, while hot, was added to ice water, and precipitated crystals were collected by filteration. The obtained crystals were air-dried and dissolved in hot acetone, and the solution was filtered to remove insoluble matter. The acetone was distilled off, and the residue was recrystallized from benzene, giving 220 mg of the title compound (yield: 51.9%).

m.p.: 253° C.

$^1$H-NMR (DMSO-d$_6$) δ: 10.60 (1H, s), 7.97 (1H, d, J=9 Hz), 7.96 (1H, d, J=7 Hz), 7.80–7.74 (2H, m), 7.59 (1H, d-d-d, J=8, 7, 1 Hz), 7.53 (1H, d, J=3 Hz), 7.44 (1H, d-d, J=9, 3 Hz)

IR(KBr)cm$^{-1}$: 2600, 2361, 1723, 1615, 1575, 1528, 1452, 1374, 1256, 1237, 1189, 859, 825, 761, 726

Reference Example 5

The following compounds were synthesized using the compounds obtained in Reference Examples 1–4.

\* 10-Chloro-3-methoxy-11H-indeno[1,2-b]quinolin-11-one m.p.: 218°–221° C.

$^1$H-NMR (CDCl$_3$) δ: 8.36 (1H, d-d, J=9, 2 Hz), 8.11 (1H, d-d, J=8, 1 Hz), 7.84–7.78 (2H, m), 7.63 (1H, d-d-d, J=9, 8, 1 Hz), 7.56 (1H, d, J=2 Hz), 7.02 (1H, d-d, J=8, 2 Hz), 4.01 (3H, s)

IR(KBr)cm$^{-1}$: 1706, 1617, 1597, 1587, 1567, 1483, 1339, 1276, 1256, 1233, 1091, 773

\* 10-Chloro-1-methoxy-11H-indeno[1,2-b]quinolin-11-one m.p.: 230°–232° C.

$^1$H-NMR (CDCl$_3$) δ: 8.37 (1H, d-d, J=8, 2 Hz), 8.12 (1H, d-d, J=8, 1 Hz), 7.81(1H, d-d-d, J=9, 8, 2 Hz), 7.73–7.60 (3H, m), 7.05(1H, d, J=8 Hz), 4.04 (3H, s)

IR(KBr)cm$^{-1}$: 1711, 1617, 1594, 1567, 1484, 1442, 1367, 1276, 1193, 1174, 1054, 1037, 948, 838, 761, 740

\* 10-Chloro-7-methoxy-11H-indeno[1,2-b]quinolin-11-one m.p.: 212°–214° C.

$^1$H-NMR (CDCl$_3$) δ: 8.23 (1H, d, J=9 Hz), 8.05 (1H, d-d, J=8, 1 Hz), 7.84 (1H, d-d, J=7, 1 Hz), 7.68 (1H, d-d-d, J=8, 8, 1 Hz), 7.53 (1H, d-d-d, J=8, 7, 1 Hz), 7.47 (1H, d, J=3 Hz), 7.24 (1H, d-d, J=9, 3 Hz), 4.01 (3H, s)

IR(KBr)cm$^{-1}$: 1714, 1612, 1584, 1573, 1504, 1349, 1225, 1137, 933, 728

EXAMPLE 1

Synthesis of 10-(((dimethylamino)ethyl)amino)-2-methoxy-11H-indeno[1,2-b]quinolin-11-one dihydrochloride (Compound 1)

A mixture of 1.2 g (4.1 mmol) of 10-chloro-2-methoxy-11H-indeno[1,2-b]quinolin-11-one obtained in Reference Example 2, 1.1 g (14.2 mmol) of N,N-dimethylethylenediamine and 20 ml of ethanol was refluxed with heating for 3 hours. After completion of the reaction, the reaction mixture was exsiccated under reduced pressure. Water was added to the residue, and the mixture was subjected to extraction with chloroform. The chloroform layer was dried with magnesium sulfate and distilled off. The residue was purified by the use of silica gel column chromatography (developing solvent; chloroform:ethanol= 20:1 (v/v)), giving 1.1 g of 10-(((dimethylamino)ethyl) amino)-2-methoxy-11H-indeno[1,2-b]quinolin-11-one (yield: 78.0%). 550 mg (1.58 mmol) of the obtained compound was dissolved in 10 ml of a mixture of tetrahydrofuran and methanol (1:1 (v/v)). The solution was made acid with 1.5 ml of 4N hydrochloric acid/dioxane. The acid solution was exsiccated under reduced pressure, and the residue was washed with diethyl ether, giving 645 mg of the title compound (yield: 96.9%, yield calculated based on the compound of Reference Example 2: 75.6%). The property values are shown in Table 1.

EXAMPLE 2

Synthesis of 10-(((dimethylamino)ethyl)amino)-2-hydroxy-11H-indeno[1,2-b]quinolin-11-one dihydrochloride (Compound 2)

15 ml of 47% aqueous hydrogen bromide was added to a solution of 550 mg (1.58 mmol) of 10-(((dimethylamino) ethyl)amino)-2-methoxy-11H-indeno[1,2-b]quinolin-11-one in 20 ml of acetic acid, and the mixture was refluxed with heating. Forty eight hours later, 10 ml of 47% aqueous hydrogen bromide was added to the reaction mixture, followed by reflux with heating for 22 hours. After completion of the reaction, the reaction mixture was exsiccated under reduced pressure. Water was added to the residue, and the mixture was made weakly basic with aqueous ammonia. Saturated saline solution was added, followed by extraction with tetrahydrofurane. The tetrahydrofuran layer was dried with magnesium sulfate and distilled off, and the residue was purified by the use of silica gel column chromatography (developing solvent; chloroform:ethanol=10:1 (v/v)). The purified product was dissolved in tetrahydrofuran, and the solution was made acid with an excess amount of 4N hydrochloric acid/dioxane and exsiccated under reduced pressure. The residue was washed with diethyl ether, giving 366 mg of title compound (yield: 56.9%). The property values are shown in Table 1.

EXAMPLE 3

Synthesis of 10-(((dimethylamino)ethyl)thio)-8-hydroxy-11H-indeno[1,2-b]quinolin-11-one (Compound 10)

A mixture of 400 mg (1.4 mmol) of 10-chloro-8-hydroxy-11H-indeno[1,2-b]quinolin-11-one, 629 mg (8.5 mmol) of lithium carbonate, 963 mg (5.7 mmol) of 2-diethylaminoethanethiol hydrochloride and 8 ml of N,N-dimethylformamide was stirred for 5 hours with heating at 90° C. After completion of the reaction, the reaction mixture was added to water, and precipitated crystals were collected by filteration. The crystals were recrystallized from ethanol, giving 310 mg of the title compound (yield: 57.7%). The property values are shown in Table 1.

EXAMPLE 4

Synthesis of 10-(((diethylamino)ethoxy)-8-hydroxy-11H-indeno[1,2-b]quinolin-11-one hydrochloride (Compound 11)

250 mg (6.3 mmol) of sodium hydride was added to a mixture of 1.77 g (15.1 mmol) of diethylaminoethanol and 20 ml of toluene with ice-cooling. The reaction mixture was returned to room temperature, stirred for 30 minutes and heated to 50° C. To the reaction mixture was added 800 mg (2.8 mmol) of 10-chloro-8-hydroxy-11H-indeno[1,2-b]quinolin-11-one, and the mixture was stirred at 60° C. for 3 hours. After completion of the reaction, saturated aqueous ammonium acetate was added to the reaction mixture, and the solvent was distilled off. Saturated aqueous sodium chloride was added to the residue, and the mixture was subjected to extraction with tetrahydrofuran. The tetrahydrofuran layer was dried with magnesium sulfate and distilled off, and the residue was purified by the use of silica gel column chromatography (developing solvent; chloroform:ethanol=10:1 (v/v)). The purified product was dissolved in 10 ml of tetrahydrofuran, and 1 ml of 4N hydrochloric acid/dioxane was added. After concentration under reduced pressure, the obtained residue was crystallized from diethyl ether, giving 203 mg of the title compound (yield: 17.9%). The property values are shown in Table 1.

EXAMPLES 5–16

Compounds 3 to 9 and 12 to 16 shown in Table 1 were prepared from the corresponding starting materials by the procedure similar to that of Examples 1 to 4.

TABLE 1

| Compound | R | Ra | Rb | Yield | m. p. | $^1$H-NMR(DMSO-$d_6$)$\delta$: | IR(KBr)cm$^{-1}$ |
|---|---|---|---|---|---|---|---|
| 1 | —NHCH$_2$CH$_2$N(CH$_3$)$_2$.2HCl | 2-OCH$_3$ | H | 75.6% | 243–247° C. (decomposition) | 10.47(1H, brs), 9.53(1H, brs), 8.78(1H, d, J=9Hz), 8.53(1H, brs), 8.24(1H, d, J=8Hz), 7.93(1H,d-d, J=8, 7Hz), 7.68(1H, d-d, J=8, 8Hz), 7.35(1H, d-d, J=9, 2Hz), 7.27(1H, d, J=2Hz), 4.48(2H, m), 3.93(3H, s), 3.50(2H, m), 2.87(6H, d, J=5Hz) | 2700, 1713, 1640, 1610, 1578, 1486, 1431, 1380, 1291, 1236, 782, 772 |
| 2 | —NHCH$_2$CH$_2$N(CH$_3$)$_2$.2HCl | 2-OH | H | 56.9% | 260–264° C. (decomposition) | 11.13(1H, brs), 10.50(1H, brs), 9.59(1H, brs), 8.80(1H, d, J=9Hz), 8.47(1H, d, J=8Hz), 8.26(1H, d, J=8Hz), 7.92(1H, d-d, J=8, 8Hz), 7.67(1H, d-d, J=8, 8Hz), 7.16–7.13(2H, m), 4.47(2H, m), 3.50(2H, m), 2.88(6H, d, J=5Hz) | 3280, 1715, 1639, 1606, 1578, 1483, 1463, 1377, 1309, 1282, 775, 761 |
| 3 | —NHCH$_2$CH$_2$N(CH$_3$)$_2$ | 3-OH | H | 62.7% | 266° C. (decomposition) | 10.56(1H, brs), 8.35(1H, d, J=8Hz), 8.14(1H, brs), 7.87(1H, d-d, J=8, 1Hz), 7.70(1H, d-d, J=7, 7, 1Hz), 7.52–7.42(2H, m), 7.22(1H, d, J=2Hz), 6.86(1H, d-d, J=8, 2Hz), 4.05(2H, m), 2.55(2H, t, J=6Hz), 2.23(6H, s) | 2820, 1668, 1614, 1584, 1533, 1503, 1480, 1472, 1461, 1316, 1266, 1187, 763 |
| 3-a | —NHCH$_2$CH$_2$N(CH$_3$)$_2$.2HCl | 3-OH | H | | 256° C. | | |
| 4 | —NHCH$_2$CH$_2$N(CH$_3$)$_2$.2HCl | H | 7-OCH$_3$ | 74.0% | 223° C. (decomposition) | 10.46(1H, brs), 9.37(1H, brs), 8.71(1H, d, J=9Hz), 8.49(1H, brd), 7.84–7.69(4H, m), 7.31(1H, d-d, J=9, 2Hz), 4.46(2H, m), 3.96(3H, s), 3.48(2H, m), 2.87(6H, d, J=5Hz) | 2700, 1708, 1642, 1625, 1602, 1575, 1505, 1465, 1270, 755 |
| 5 | —NHCH$_2$CH$_2$N(CH$_3$)$_2$.2HCl | H | 7-OH | 69.4% | 232–234° C. (decomposition) | 10.45(1H, brs), 9.38(1H, brs), 8.65(1H, d, J=9Hz), 8.58(1H, brd), 7.84–7.66(4H, m), 7.16(1H, d, J=7Hz), 4.46(2H, m), 3.50(2H, m), 2.87(6H, d, J=5Hz) | 3050, 2700, 1714, 1642, 1572, 1508, 1362, 755 |
| 7 | —NHCH$_2$CH$_2$CH$_2$N(CH$_3$)$_2$ | H | 7-OH | 63.5% | 242–245° C. | 8.30(1H, t, J=6Hz), 8.13(1H, d, J=9Hz), 7.84(1H, d-d, J=7, 1Hz), 7.65–7.60 (2H, m), 7.51(1H, d-d, J=8, 7Hz), 7.14(1H, d, J=3Hz), 6.95(1H, d-d, J=9, 3Hz), 3.97(2H, d-t, J=6, 7Hz), 2.35(2H, t, J=7Hz), 2.15(6H, s), 1.79(2H, m) | 3300, 2940, 1662, 1615, 1593, 1568, 1496, 1483, 1467, 1448, 1380, 1263, 1253 |
| 7-a | —NHCH$_2$CH$_2$CH$_2$N(CH$_3$)$_2$.2HCl | H | 7-OH | | 251° C. (decomposition) | | |

TABLE 1-continued

| Compound | R | Ra | Rb | Yield | m. p. | $^1$H-NMR(DMSO-$d_6$)δ: | IR(KBr)cm$^{-1}$ |
|---|---|---|---|---|---|---|---|
| 8 | —N(CH$_3$)CH$_2$CH$_2$N(C$_2$H$_5$)$_2$.2HCl | H | 7-OCH$_3$ | 87.1% | 229~233° C. | 10.66(1H, brs), 8.43(1H, d, J=7Hz), 8.31(1H, d, J=9Hz), 7.80–7.66(4H, m), 7.27(1H, d-d, J=9, 3Hz), 4.24(2H, m), 3.98(3H, s), 3.42–3.40(2H, m), 3.09(4H, m), 1.19(6H, t, J=7Hz) | 3450, 1715, 1639, 1615, 1570, 1492, 1358, 432, 406 |
| 9 | —N⌒N—Ph | H | 7-OCH$_3$ | 81.7% | 258~261° C. | 8.13(1H, d, J=9Hz), 7.92(1H, d-d, J=7, 2Hz), 7.73–7.68(2H, m), 7.57(1H, d-d-d, J=8, 7, 2Hz), 7.42(1H, d, J=3Hz), 7.31–7.25(2H, m), 7.15(1H, d-d, J=9, 3Hz), 7.08–7.05 (2H, m), 6.84(1H, d-d, J=7, 7Hz), 3.96(3H, s), 3.81(2H, m), 3.44(2H, m) | 2820, 1698, 1608, 1581, 1563, 1500, 1447, 1417, 1349, 1234, 1218, 1124, 932, 762, 726 |
| 10 | —SCH$_2$CH$_2$N(C$_2$H$_5$)$_2$ | H | 8-OH | 57.7% | 213~216° C. | 7.97–7.91(3H, m), 7.78–7.72(2H, m), 7.57(1H, d-d-d, J=8, 7, 1Hz), 7.38(1H, d-d, J=9, 2Hz), 3.38(2H, t, J=7Hz), 2.61(2H, t, J=7Hz), 2.40(4H, q, J=7Hz), 0.82(6H, t, J=7Hz), | 2970, 2360, 2340, 2330, 1704, 1613, 1573, 1569, 1525, 1480, 1469, 1463, 1454, 1390, 1380, 1372, 1243, 724 |
| 10-a | —SCH$_2$CH$_2$N(C$_2$H$_5$)$_2$.HCl.3/2H$_2$O | H | 8-OH | | 164~168° C. | | |
| 11 | —OCH$_2$CH$_2$N(C$_2$H$_5$)$_2$.HCl | H | 8-OH | 17.9% | 280° C.< | 10.28(1H, brs), 8.00(1H, d, J=8Hz), 7.90(1H, d, J=9Hz), 7.80–7.74(2H, m), 7.62–7.57(2H, m), 7.41(1H, d-d, J=9, 3Hz), 5.18(2H, t, J=4Hz), 3.72(2H, m), 3.32(4H, m), 1.32(6H, t, J=7Hz) | 2640, 1724, 1639, 1610, 1583, 1539, 1466, 1388, 1327, 1255, 1237 |
| 12 | —NHCH$_2$CH$_2$N(CH$_3$)$_2$.2HCl | H | 8-OH | 60.8% | 235~239° C. (decompotion) | 10.63(1H, brs), 10.34(1H, brs), 8.49(1H, brs), 8.15(1H, d, J=8Hz), 7.96(1H, s), 7.84–7.68(4H, m), 7.52(1H, d, J=7Hz), 4.47(2H, m), 3.50–3.48(2H, m), 2.86(6H, d, J=5Hz) | 3370, 2700, 1706, 1639, 1626, 1600, 1577, 1534, 1467, 1378, 757 |
| 13 | —N⌒N—CH$_3$.2HCl | H | 8-OCH$_3$ | 51.5% | 243~246° C. | 10.86(1H, brs), 8.12–8.05(2H, m), 7.79–7.73(2H, m), 7.64–7.58(1H, m), 7.53(1H, d-d, J=9, 3Hz), 7.41(1H, d, J=3Hz), 3.99(3H, s), 3.93(4H, m), 3.48(4H, m), 2.93(3H, d, J=5Hz) | 2610, 1726, 1639, 1562, 1537, 1484, 1469, 1451, 1388, 1285, 1251, 1241 |
| 14 | —N⌒N—CH$_3$.2HCl | H | 8-OH | 70.8% | 260° C. (decomposition) | 10.79(1H, brs), 8.08(1H, d, J=8Hz), 7.98(1H, d, J=9Hz), 7.77–7.72(2H, m), 7.60(1H, d-d, J=8, 8Hz), 7.47(1H, d, J=3Hz), 7.38(1H, d-d, J=9, 3Hz), 3.97–3.87(4H, m), 3.55–3.43(4H, m), 2.93(3H, d, J=4Hz) | 3360, 1702, 1634, 1543, 1465, 1379, 1261 |
| 15 | —NHCH$_2$CH$_2$N⌒ | H | 8-OH | 56.9% | 225~228° C. | 9.98(1H, brs), 8.07(1H, brs), 7.83 (1H, d, J=8Hz), 7.73(1H, d, J=9Hz), 7.68–7.60(3H, m), 7.49(1H, d-d-d, J=8, 7, 1Hz), 7.26(1H, d-d, J=9, 2Hz), 4.11(2H, m), 2.85(2H, brs), 2.66(4H, brs), 1.75(4H, brs) | 3320, 1683, 1585, 1552, 1318, 1250, 1182 |
| 6 | —NHCH$_2$CH$_2$CH$_2$N(CH$_3$)$_2$ | H | 7-OCH$_3$ | 70.9% | 117~119° C. | 8.61(1H, brs), 8.03(1H, d, J=9Hz), 7.93(1H, d, J=7Hz), 7.67(1H, d, J=7Hz), 7.55(1H, d-d-d, J=7, 7, 1Hz), 7.43(1H, d-d-d, J=7, 7, 1Hz), 7.38(1H, d, J=3Hz), 6.97(1H, d-d, J=9, 3Hz), 3.98(2H, m), 3.96(3H, s), 2.54(2H, t, J=7Hz), 2.31(6H, s), 1.96(2H, m, J=7Hz) | 2770, 1666, 1623, 1615, 1592, 1500, 1478, 1466, 1455, 1433, 1337, 1232, 1167, 1146, 1023, 728 |

TABLE 1-continued

[Structure: indeno-quinolinone core with R at position 9, O at top, Ra on benzene ring (positions 1-4), Rb on other ring (positions 6-9), N at position 5]

| Compound | R | Ra | Rb | Yield | m. p. | $^1$H-NMR(DMSO-$d_6$)δ: | IR(KBr)cm$^{-1}$ |
|---|---|---|---|---|---|---|---|
| 16 | —N(piperidine)—N(piperidine)— | H | 8-OH | 33.8% | 221° C. (decomposition) | 7.97(1H, d, J=8Hz), 7.91(1H, d, J=9Hz), 7.68(1H, d, J=7Hz), 7.59–7.38(3H, m), 7.27(1H, d-d, J=8, 2Hz), 3.59–3.57(3H, m), 2.72(6H, brs), 2.07–1.86(2H, m), 1.72(4H, brs), 1.49(2H, brs), 1.25(2H, brs) | 3410, 2930, 1699, 1615, 1578, 1529, 1461, 1452, 1369, 1245 |
| 16-a | —N(piperidine)—N(piperidine)— .2HCl.7/4H$_2$O | H | 8-OH | | 264–267° C. | | |

Pharmacological Test Example 1
Cytocidal Effect

A 96-well plate was innoculated with 2×10$^3$ cells/well of P 388 mouse leukemia cell line. The compound of the present invention was dissoved in purified water or dimethylsulfoxide, and the solution was diluted with medium to various concentrations and placed into respective wells and incubated. After three day's incubation, the plate was fixed with glutaraldehyde and stained with crystal violet for cytometry.

The cytocidal effect of each compound was expressed as the concentration at which the cell count is 50% less than that of the control (IC$_{50}$). The results are shown in Table 2.

TABLE 2

| Compound No. | IC$_{50}$ (µg/ml) |
|---|---|
| 1 | 3.4 × 10$^{-1}$ |
| 2 | 1.5 × 10$^{-1}$ |
| 3-a | 1.5 × 10$^{-1}$ |
| 4 | 2.5 × 10$^{-1}$ |
| 5 | 5.2 × 10$^{-2}$ |
| 7-a | 1.6 × 10$^{-1}$ |
| 10-a | 4.2 × 10$^{-1}$ |
| 11 | 9.6 × 10$^{-2}$ |
| 12 | 1.6 × 10$^{-1}$ |
| 13 | 3.7 × 10$^{-1}$ |
| 14 | 2.2 × 10$^{-1}$ |
| 16-a | 4.3 × 10$^{-1}$ |

Preparation Example 1
Capsules

According to the following formula, capsuls were parepared by a conventional process.

| | |
|---|---|
| Compound 1 | 200 mg |
| Lactose | 30 mg |
| Corn starch | 50 mg |
| Crystalline cellulose | 10 mg |
| Magnesium stearate | 3 mg |
| Per capsule | 293 mg |

Preparation Example 2
Tablets

According to the following formula, tablets were parepared by a conventional process.

| | |
|---|---|
| Compound 2 | 100 mg |
| Lactose | 47 mg |
| Corn starch | 50 mg |
| Crystalline cellulose | 50 mg |
| Hydroxypropyl cellulose | 15 mg |
| Talc | 2 mg |
| Magnesium stearate | 2 mg |
| Ethyl cellulose | 30 mg |
| Unsaturated fatty acid glyceride | 2 mg |
| Titanium dioxide | 2 mg |
| Per tablet | 300 mg |

Preparation Example 3
Granules

According to the following formula, granules were parepared by a conventional process.

| | |
|---|---|
| Compound 3-a | 200 mg |
| Mannitol | 540 mg |
| Corn starch | 100 mg |
| Crystalline cellulose | 100 mg |
| Hydroxypropyl cellulose | 50 mg |
| Talc | 10 mg |
| Per packet | 1000 mg |

Preparation Example 4
Fine granules

According to the following formula, fine granules were prepared by a conventional process.

| | |
|---|---|
| Compound 5 | 200 mg |
| Mannitol | 520 mg |
| Corn starch | 100 mg |
| Crystalline cellulose | 100 mg |

-continued

| | |
|---|---|
| Hydroxypropyl cellulose | 70 mg |
| Talc | 10 mg |
| Per packet | 1000 mg |

Preparation Example 5

Injection

According to the following formula, an injection was parepared by a conventional process.

| | |
|---|---|
| Compound 7-a | 100 mg |
| Distilled water for injections | q.s. |
| Per ample | 2 ml |

Preparation Example 6

Suppositories

According to the following formula, suppositories were prepared by a conventional process.

| | |
|---|---|
| Compound 11 | 200 mg |
| Witepsol S-55 (a mixture of mono-, di- and triglycerides of saturated fatty acids from lauric acid to stearic acid, product of Dynamite Nobel) | 1300 mg |
| Per suppository | 1500 mg |

We claim:

1. A condensed indan derivative represented by the formula (1)

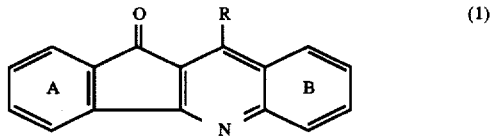

(1)

wherein the ring A is an optionally substituted benzene ring or a benzene ring which has lower alkylenedioxy group(s), the ring B is an optionally substituted benzene ring or a benzene ring which has lower alkylene dioxy group(s), and R is a group —$NR_1R_2$, an optionally substituted nitrogen-containing heterocyclic group, a group —$OR_3$ or a group —$SR_4$ (wherein $R_1$ and $R_2$ are the same or different and each represent a hydrogen atom, a phenyl group, an optionally substituted nitrogen-containing heterocyclic group, or a lower alkyl group which may be substituted by optionally substituted amino group(s), lower alkoxy group(s), phenyl group(s), nitrogen-containing heterocyclic group(s) or hydroxyl group(s), and $R_3$ and $R_4$ each represent a lower alkyl group which may be substituted by substituted amino group(s)), provided that at least one of the rings A and B is a substituted benzene ring and R is not —$NHCH_3$, $NH_2$, $NHCH_2CH_2OH$, —NHPh, —$N(CH_3)_2$, —$N(CH_3)Ph$, or piperidine, or a salt thereof.

2. A condensed indan derivative or a salt thereof according to claim 1 wherein the rings A and B are the same or different and each represent a benzene ring which may have lower alkoxy group(s) or hydroxyl group(s), R is a group —$NR_1R_2$, an optionally substituted nitrogen-containing heterocyclic group, a group —$OR_3$ or a group —$SR_4$.

3. A condensed indan derivative or a salt thereof according to claim 2 wherein R is a group —$NR_1R_2$ (wherein $R_1$ and $R_2$ are the same or different and each represent a hydrogen atom or a lower alkyl group which may be substituted by a di-lower alkyl-substituted amino group or a pyrrolidinyl group), a lower alkyl- or phenyl-substituted piperazinyl group, a piperidino-substituted piperidino group, a group —$OR_3$ or a group —$SR_4$ (wherein $R_3$ and $R_4$ each represent a lower alkyl group which may be substituted by a di-lower alkyl-substituted amino group).

4. A condensed indan derivative or a salt thereof according to claim 3 wherein R is a group —$NR_1R_2$ (wherein $R_1$ is a lower alkyl group substituted by a di-lower-alkyl substituted amino group or a pyrrolidinyl group, and $R_2$ is a halogen atom).

5. A condensed indan derivative or a salt thereof according to claim 1 wherein the ring A is an unsubstituted or hydroxyl-substituted benzene ring.

6. A condensed indan derivative or a salt thereof according to claim 1 wherein the ring B is an unsubstituted or hydroxyl-substituted benzene ring.

7. A composition comprising an effective amount of a condensed indan derivative or a salt thereof according to claim 1 and pharmaceutical carrier(s).

8. A method for producing a condensed indan derivative of the formula (1) according to the following reaction scheme:

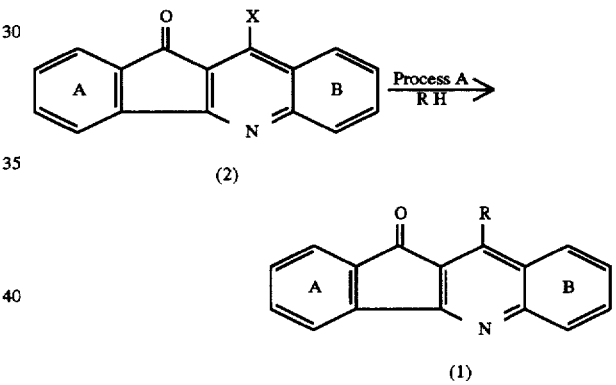

wherein the ring A is an optionally substituted benzene ring or a benzene ring which has lower alkylenedioxy group(s), the ring B is an optionally substituted benzene ring or a benzene ring which has lower alkylenedioxy group(s), X is a halogen atom, R is a group —$NR_1R_2$, an optionally substituted nitrogen-containing heterocyclic group, a group —$OR_3$ or a group $SR_4$, RH is an amine, alcohol ($R_3OH$) or thiol ($R_4SH$) (wherein $R_1$ and $R_2$ are the same or different and each represent a hydrogen atom; a phenyl group; an optionally substituted nitrogen-containing heterocyclic group; or a lower alkyl group which may be substituted by optionally substituted amino group(s), lower alkoxy group (s), phenyl group(s), nitrogen-containing heterocyclic group (s) or hydroxyl group(s), and $R_3$ and $R_4$ each represent a lower alkyl group which may be substituted by substituted amino group(s), provided that at least one of the rings A and B is a substituted benzene ring and R is not $NHCH_3$, $NH_2$, $NHCH_2CH_2OH$, —NHPh, —$N(CH_3)_2$, —$N(CH_3)Ph$, or piperidine.

* * * * *